United States Patent [19]

Welker

[11] Plant 4,504

[45] Feb. 19, 1980

[54] DIEFFENBACHIA PLANT

[76] Inventor: Richard P. Welker, P.O. Box 637, Apopka, Fla. 32703

[21] Appl. No.: 938,976

[22] Filed: Aug. 31, 1978

[51] Int. Cl.[2] ..... A01H 5/12

[52] U.S. Cl. ..... Plt./88

[58] Field of Search ..... Plt./88

[56] References Cited

PUBLICATIONS

Tropica, Graf, 1978, Roehrs Co., E. Rutherford, N.J., pp. 106–108, 988.

*Primary Examiner*—Robert E. Bagwill

*Attorney, Agent, or Firm*—Roger L. Martin

[57] ABSTRACT

A new and distinct plant variety of the Arum Family has a growth habit providing specimens which exhibit a compact growth habit with frequent tillering, leaf blades having a mottled generally achlorophyllous center field that is extensive by comparison to those of the 'Perfection' and 'Exotica' varieties and provided with achlorophyllous streaks that follow the pattern of the lateral secondary veins, and with chlorophyllous blotches and flecks that include colors found in a narrow border area surrounding the center field. The petioles of the leaf have a basal sheathing portion with a distal termination that characteristically is located closer to the leaf blade than to the petiole insertion at blade maturity.

3 Drawing Figures

This invention relates to a new and distinct plant variety of the Arum Family and which has been developed from a sport that appeared on a plant specimen of the *Dieffenbachia sequine* 'Perfection' variety that is known horticulturally as Dieffenbachia 'Exotica Perfection'. The specimen was under cultivation in a nursery at Apopka, Fla. at the time of the discovery and since then, the new variety has been asexually reproduced at the same nursery and by the propagation of stem cuttings taken from the sport.

Plant specimens of the 'Perfection' variety are related to the Dieffenbachia 'Exotica' variety. The 'Exotica' and 'Perfection' varieties are both variegated and provided with a more or less achlorophyllous mottled center field that is surrounded by a chlorophyllous border, the border being wider and the center field being substantially smaller than those of the variety forming the subject matter of this application. Apart from the above, the variety forming the subject matter of this application has a center field which is lighter and generally whiter than those of the 'Perfection' and 'Exotica' varieties. Other known related varieties having an achlorophyllous center field are equipped with patterns of variegation and/or chlorophyllous border areas that differ from those of the instant variety either in pattern, blotch and/or fleck sizes, border size, or color, or one or more thereof. One objective of the invention has been to develop a new variety of the Arum Family for the foliage plant market and which is distinguishable from known varieties of this family. This objective has been fully realized by the invention as will be apparent form the following plant description contained herein and where it will be seen that the new plant variety is distinguishable from its antecedents and known related varieties by a growth habit which provides specimens having:

1. A compact growth habit with frequent tillering,
2. Leaf blades having a mottled generally achlorophyllous center field that is extensive by comparison to those of the 'Perfection' variety and provided with achlorophyllous streaks that follow the pattern of the lateral secondary veins, and with chlorophyllous blotches and flecks that tend to concentrate along and include colors found in a narrow border area surrounding the center field, and
3. Petioles that have a basal sheathing portion with a distal termination that characteristically is located closer to the leaf blades than to the petiole insertion at blade maturity.

The accompanying drawings serve by color photographic means to illustrate the new variety, one sheet showing a single plant specimen of the new variety while the other sheet provides a photographic close-up of a spathe and spadix of the variety and yet another photograph of the spathe and spadix as seen with surrounding foliage.

The following is a detailed description of the new variety and is based on observations of well fertilized specimens which were grown in the central Florida area under 70% shaded nursery conditions and where temperatures are generally maintained in the range from about 18° C. to about 30° C. during the winter months and from about 24° C. to about 36° C. during the summer months. The description is further based on observations of specimens that were 3–9 months in age.

Except where general terms of ordinary dictionary significance are obviously used, color terminology and color designations reported herein are in accord with the ISCC-NBS Method of Designating Colors as described in the U.S. Department of Commerce, National Bureau of Standards, Circular 553, entitled ISCC-NBS "Method of Designating Colors and Dictionary of Colored Names" with the color designations having been derived through interpretation of Munsell Color Notations obtained by comparing plant specimens with color specimens in the current "Neighboring Hues Edition" published by Munsell Color Company, Inc. of Baltimore, Md., and to which the reported color notations (Munsell Hue, Munsell Value/Munsell Chroma) are referenced.

PLANT DESCRIPTION

Name: *Dieffenbachia sequine* 'Welkeri Compacta'.

Origin: Sport or bud variation that appeared on a specimen of the variety known as *Dieffenbachia sequine* 'Perfection'.

Classification:

A. *Botanic.*—*Dieffenbachia sequine* (Jacquine) Schott. Arum Family (Araceae).

B. *Commercial.*—Foliage plant.

Form: Herbaceous, tropical, perennial evergreen with adventitious root system, erect primary axis and frequent tillering, and erecto-patent leaves.

Stem:

A. *General.*—Caulescent erect and herbaceous with a firm epidermis and corticated with a subepidermal rind.

B. *Texture.*—Moderately rugose (at 10 × magnification) with scattered, whitish, wax-like surface particles that diminish in concentration as the surface area matures.

C. *Size.*—(1) Diameter: Commonly 1.5–2.5 cm. in the exposed basal internode area next adjacent soil line for specimens 3–9 months in age. (2) Internode length: Usually shortest at base and commonly 1.5–2.5 cm. between fully developed nodes in specimens 3–9 months in age.

D. *Color.*—(1) General: A mottled background with small dark patches appearing that are usually elongated and arranged longitudinally of the stem. (2) Background color: Commonly moderate yellow green (near 7.5 GY 5/4) and/or moderate yellowish green (10 GY 5/4). (3) Patch color: Commonly dark yellowish green (near 10 GY 4/4), moderate olive green (near 7.5 GY 3/4) (7.5 GY 4/4) and/or moderate yellowish green (10 GY 6/4) (10 GY 5/4).

Leaves:

A. *General.*—Simple, complete pericladial petiole with the basal sheathing portion being winged by lateral stipules.

B. *Arrangement.*—Alternate with 2/5 phyllotaxy.

C. *Margins.*—Entire with undulate tendencies.

D. *Venation.*—(1) General: Pinnate with a prominent midrib, secondary lateral veins that are imbedded at the adaxial side of the leaf blade and prominent at the abaxial side of the leaf blade, tertiary lateral veins that are parallel to the secondary veins and imbedded at both the abaxial and adaxial sides of the leaf blade, the secondary and tertiary veins being joined by cross veins that provide a scalariform arrangement. (2) Shape and arrangement: (a) Midrib — tapering distally, flattened at the adaxial side of the leaf blade and thereat being half-oblong in cross section, and prominently keeled at the abaxial side of the leaf blade and thereat being half-circular to half elliptic in cross section, the flattened surface usually having 12 to 19 conspicuous (at 10 × magnification) longitudinally extending low ridges formed by vascular strands and the keel usually having 17 to 25 conspicuous (at 10 × magnification) longitudinally extending low ridges formed by vascular strands that are more widely spaced at the summit than on the slopes of the keel. (b) Lateral veins — usually 9–18 secondary veins branching from each side of the midrib and at intervals that are of commonly 10–20 mm. and with the tertiary veins being commonly spaced at intervals in the range of about 1–2 mm. (3) Midrib color: (a) General — concolorous with petiole at base of midrib on adaxial blade side and abruptly lightening distally of the concoloration, the flattened surface being frequently provided with small scattered striate patches that are usually lacking at the distal end of the midrib, and the basal end of the keel being usually concolorous with the petiole on the abaxial blade side. (b) Adaxial side — commonly white (near 2.5 GY 9/0), yellowish white (2.5 GY 9/1), pale yellow green (2.5 GY 9/2) (near 5 GY 9/2) and/or greenish white (5 GY 9/1) distally of petiole concoloration, and moderate yellow green (near 5 GY 6/6) (7.5 GY 6/6) and/or moderate yellowish green (near 10 GY 6/6) in patched areas. (c) Abaxial side — commonly light yellow green (near 5 GY 8/4) (5 GY 8/6) and/or moderate yellow green (2.5 GY 7/6) at the keel summit and moderate olive green (near 7.5 GY 3/4) and/or dark yellowish green (10 GY 3/4) at the base of the slopes. (4) Secondary vein color: (a) General — generally achlorophyllous on adaxial side and appearing as lateral streaks in center field of leaf blades. (b) Adaxial side — commonly white (near 2.5 GY 9/0), yellowish white (2.5 GY 9/1), pale yellow green (2.5 GY 9/2) (near 5 GY 9/2) and/or greenish white (5 GY 9/1).

E. *Shape.*—(1) General: Asymmetric but generally elliptic to ovate and occasionally showing oblong tendencies. (2) Leaf apices: Attenuated acuminate to cuspidate with a canaliculate tip that commonly terminates in an evanescent vestige that is usually dead. (3) Leaf bases: Asymmetric but generally cordate with the larger basal lobe tending to be decurrent.

F. *Petioles.*—(1) General: Elongated, fleshy, pericladial and winged with adnate ligulate stipules along sheathing basal portion that is provided with a stem-encircling portion at the transverse petiole insertion, the sheathing basal portion having a distal termination that is characteristically located closer to the leaf blade than to the petiole insertion in mature leaves. (2) Shape: Generally elongated with distally attenuating unpigmented translucent, stipular wings that terminate in a membraneous, transverse ligule which provides a broadly acute to obtuse distal termination for the sheathing basal portion, the petiole basal portion being generally bulbous, and the adaxial side distally of the petiole basal portion being planar to slightly concave and bounded by a pair of longitudinally extending translucent hyaline ridges. (3) Texture: Glabrous and striately ridged. (4) Size: (6 to 9 month specimens) (a) Width — commonly 4 to 7 mm. distally of and adjacent to ligule. (b) Depth — commonly 4 to 7 mm. distally of and adjacent to ligule. (c) Length (insertion to leaf base) — commonly 13 to 18 cm. for mature leaves located generally intermediate the proximal and distal ends of stem. (5) Color: Commonly light yellow green (5 GY 8/4) (near 5 GY 8/6), moderate yellow green (near 2.5 GY 7/6) (5 GY 6/6) (near 7.5 GY 6/6) and/or strong yellow green (5 GY 6/8).

G. *Leaf blades.*—(1) General: Chartaceous laterally of midrib and between secondary veins. (2) Texture: (a) Upper epidermis — glabrous and somewhat sulcate along secondary veins. (b) Lower epidermis — glabrous and glaucous, and ridged along secondary veins. (3) Size: (a) Length — commonly 15–30 cm. between proximal and distal ends. (b) Width — commonly 7–15 cm. intermediate proximal and distal ends. (4) Color: (a) General — variegated with a mottled center field having generally achlorophyllous lateral streaks which follow the secondary veins and irregular chlorophyllous blotches and flecks which tend to concentrate along and merge with a narrow surrounding border that is generally continuous along the blade margins, the colors and patterns being somewhat obscured at the abaxial side of the blade by the translucent lower epidermis and the glaucous nature thereof. (b) Border — commonly dark green (5 G 3/4) (7.5 G 3/4), dark yellowish green (2.5 G 3/4) (10 GY 3/4) (10 GY 4/4), moderate olive green (7.5 GY 3/4) (7.5 GY 4/4) (5 GY 4/4), moderate yellow green (near 7.5 GY 5/4) (near 7.5 GY 5/6) (5 GY 5/4) (near 5 GY 5/6). (c) Center field — (1) Background: Commonly white (2.5 GY 9/0), yellowish white (near 10 Y 9/1), greenish white (5 GY 9/1), pale yellow green (2.5 GY 9/2) (5 GY 9/2) (near 10 Y 9/2), pale greenish yellow (near 10 Y 9/4) (near 7.5 Y 9/4) light yellow green (near 2.5 GY 8/6) (near 5 GY 9/6) and/or brilliant yellow green (near 5 GY 8/8). (2) Streaks: (a) General — generally achlorophyllous on adaxial side and appearing as lateral streaks in center field of leaf blades. (b) Adaxial side — commonly white (near 2.5 GY 9/0), yellowish white (2.5 GY 9/1), pale yellow green (2.5 GY 9/2) (near 5 GY 9/2) and/or greenish white (5 GY 9/1). (3) Blotches and flecks: Commonly dark green (5 G 3/4) (7.5 G 3/4), dark yellowish green (2.5 G 3/4) (10 GY 3/4) (10 GY 4/4), moderate olive green (7.5 GY 3/4) (7.5 GY 4/4) (5 GY 4/4), strong yellow green (near 2.5 GY 7/8) (near 5 GY 7/8) (5 GY 7/10) (near 5 GY 6/8) and/or moderate yellow green (near 5 GY 7/6) (near 7.5 GY 5/4) (near 7.5 GY 5/6) (5 GY 5/4) (near 5 GY 5/6).

Inflorescence form: Axillary spathe and spadix located adaxially to a normal leaf and abaxially of a single membraneous bract.

Peduncle:

A. *General.*—Succulent.

B. *Texture.*—Smooth and glabrous.

C. *Shape.*—Terete.

D. *Size.*—(1) Length: Commonly 3–5.5 cm. (2) Diameter: Usually 5–7 mm.

E. *Color.*—Usually moderate yellow green (near 5 GY 6/6) (near 7.5 GY 6/6) and/or strong yellow green (near 5 GY 6/8).

Spathe:

A. *General.*—Succulent, tightly inrolled both prior to and after flowering and adnate to spadix, the distal portion of the spathe being free of the staminate spike and reflexing in the larger inflorescences during the period of pollen presentation.

B. *Texture.*—Smooth and glabrous.

C. *Size.*—(1) Length: Commonly 12–25 cm. (2) Diameter (maximum): Usually 1–3 cm.

D. *Color.*—Commonly moderate yellow green (near 5 GY 5/6) (near 7.5 GY 5/6) and/or pale greenish yellow (near 10 Y 9/4) (near 7.5 Y 9/4).

Pedicels: Lacking

Flowers:

A. *General.*—Incomplete and imperfect with staminate flowers being born distally on the spadix in a free strobiloid spike, pistillate flowers being born proximally on the spadix in a loose aggregation that is spaced from the staminate flowers by a nearly naked axis region, the spadix being adnate to spathe proximally of the naked area.

B. *Size.*—(1) Spadix — (a) Diameter: Commonly 8–13 mm. in staminate flower area. (b) Length: Commonly 10–20 cm. with staminate flower area usually 4–8.5 cm. in length pistillate flower area usually between 5–8 cm. in length, and naked area between 2–4 cm. in length. (2) Staminate flower — (a) Diameter: Usually 2–3 mm. (3) Pistillate flower — (a) Diameter: Usually 5–9 mm.

C. *Calyx.*—Lacking.

D. *Corolla.*—Lacking.

E. *Androecium.*—(1) General: Anthers bilocular and suspended from a usually hexagonal pedestal which is valvate to other flowers prior to aestivation. (2) Number of flowers: Commonly 90–200 staminate florets. (3) Length of anthers: About 1.8–2.0 mm. (4) Color: (a) Anthers — usually yellowish white (near 10 YR 9/1) (near 10 YR 9/2) (near 2.5 Y 9/2), pale yellow (near 2.5 Y 9/2) and/or pale orange yellow (near YR 9/2) at time of pollen presentation. (b) Pollen — translucent white (near 10 YR 9/0), and/or yellowish white (near 10 YR 9/1).

F. *Gynoecium.*—(1) General: Compound pistil with 2–3 carpels subtended by usually three staminodia. (2) Stigma: (a) General — capitate to weakly lobed. (b) Size — 2–2.5 mm. in diameter. (c) Color — usually vivid yellow (near 2.5 Y 8/2) (near 5 Y 8/12), brilliant yellow (near 2.5 Y 8/10), and/or strong yellow (near 2.5 Y 8/10). (3) Style: Lacking. (4) Ovary: (a) General — superior, 2–3 carpellate with basal placentation and 1–2 globular ovules per carpel. (b) Size — 2.5–3.0 mm. in diameter. (c) Color — Moderate yellow green (near 5 GY 5/6) (near 7.5 GY 5/6).

Growth Habit: Erect, compact with frequent tillering and vigorous.

The following is a general description of a specimen of the new plant variety which was grown in a nursery in Apopka, Fla., from the propagation of a stem cutting containing one node, the description being taken in May.

Age of specimen: 3 months from initial propagation.

Height of plant with leaves: 46 cm.

Number of nodes: 8.

Number of expanded leaves: 7.

Number of leaves in vernation: 1.

A. *Stem.*—(1) Diameter — ranges from about 18 mm. near the soil line to about 16 mm. at the highest exposed internode. (2) Height of stem — ranges about 15 cm. from the soil line to the side of the apical meristem. (3) Internode distance — 2.8 cm. (average). (4) Color — moderate yellow green (7.5 GY 5/4) and moderate yellowish green (10 GY 5/4) in background with dark yellowish green (10 GY 4/4), moderate olive green (7.5 GY 3/4) and moderate yellowish green (10 GY 6/4) (10 GY 5/4) in patches.

B. *Leaves.*—(1) Petiole — (a) Diameter: About 4 mm. on smaller leaves and about 7 mm. on larger leaves. (b) Length: 13–15 cm. and averaging about 13–14 cm. for the specimen. (c) Color: Moderate yellow green (5 GY 6/6) (7.5 GY 6/6) and strong yellow green (5 GY 6/8). (2) Leaf blades — (a) Length: 18–25 cm. (b) Width (maximum): 7.5–12.5 cm. (c) Color: (1) Border — dark yellowish green (10 GY 3/4), moderate olive green (near 7.5 GY 3/4) (5 GY 4/4), moderate yellow green (near 7.5 GY 5/4) (near 7.5 GY 5/6) (near 5 GY 5/4) (near 5 GY 5/6). (2) Center field — (a) Background: Light yellow green (2.5 GY 8/6) (5 GY 9/6), brilliant yellow green (near 5 GY 9/8), white (near 2.5 GY 9/0), yellowish white (2.5 GY 9/1), greenish white (near 5 GY 9/1), pale greenish yellow (near 10 Y 9/1) (near 7.5 Y 9/4) pale yellow green (near 10 Y 9/2) yellowish white (10 Y 9/1). (b) Streaks: Yellowish white (2.5 GY 9/1) pale yellow green (2.5 GY 9/2) and greenish white (5 GY 9/1). (c) Blotches and flecks: Strong yellow green (2.5 GY 7/8) (5 GY 7/8) (5 GY 7/10) (5 GY 6/8), moderate yellow green (5 GY 7/8) dark green, (5 G 3/4), and dark yellowish green (10 GY 3/4).

Habit: The stem is erect from the buried cutting with leaf petioles being erecto-patent at an angle of 20° to 30° from perpendicular and the leaf blades reflexed at the petiolar junction at angles of 30° to 60° from the axis and tendency to turn downward.

I claim:

1. The new and distinct variety of the Arum Family, substantially as herein shown and described.

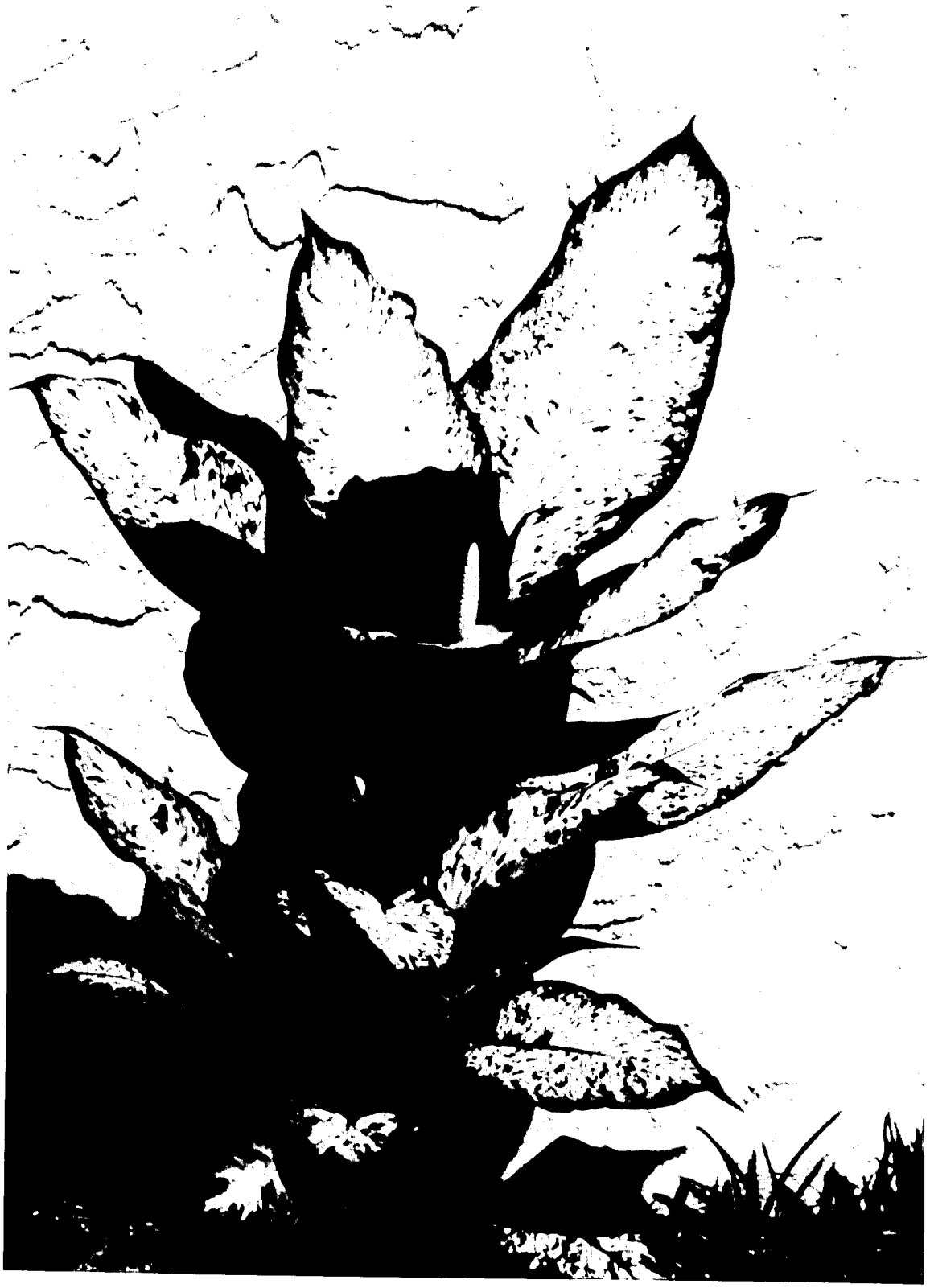

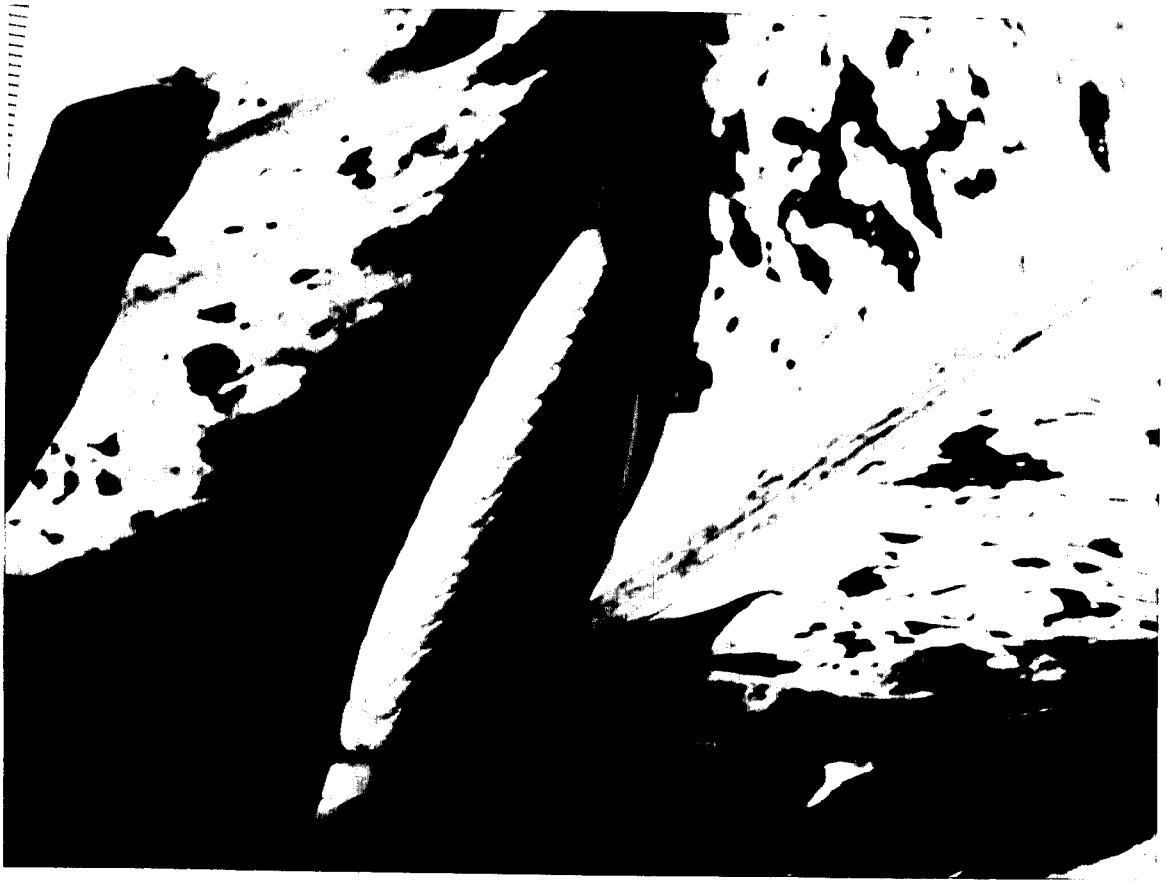
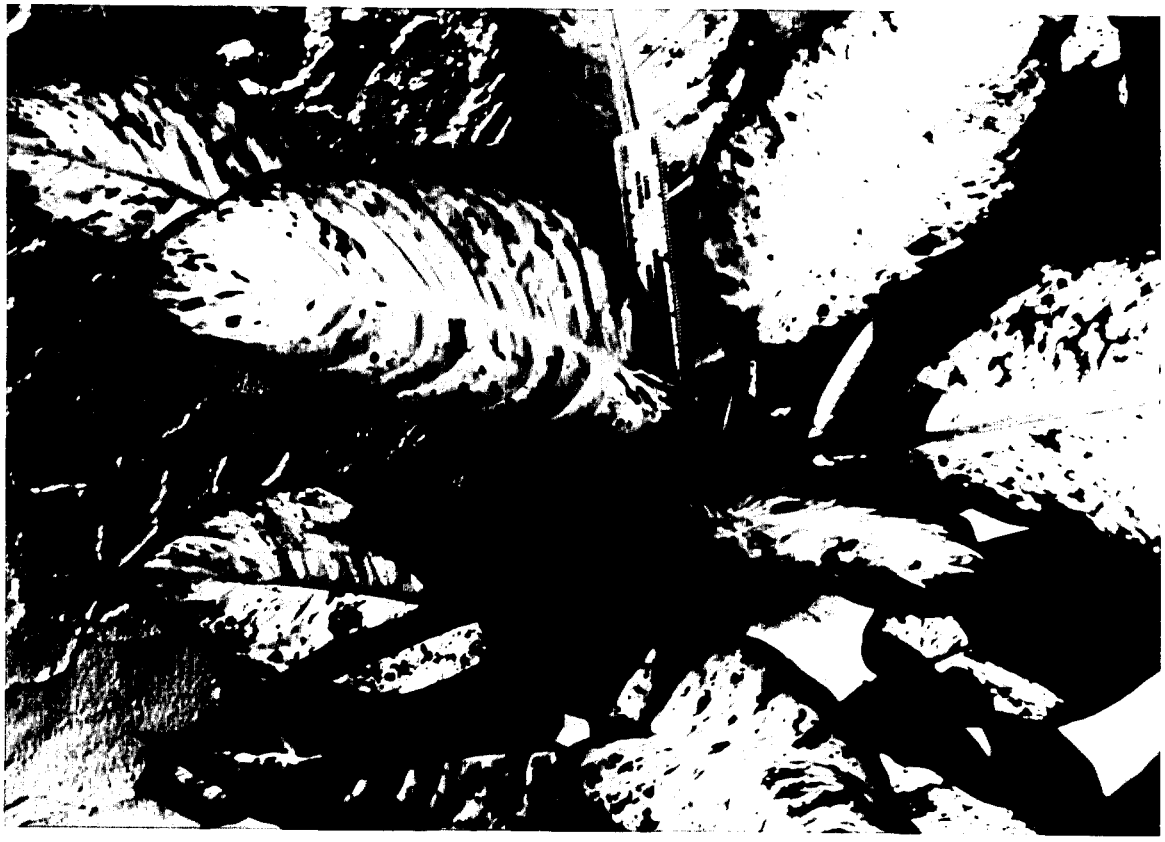

* * * * *